United States Patent [19]
Kato et al.

[11] Patent Number: 6,084,074
[45] Date of Patent: *Jul. 4, 2000

[54] STABILIZED AQUEOUS LIQUID PREPARATIONS OF BLOOD COAGULATION FACTOR XIII

[75] Inventors: Naoko Kato, Saitama; Shuji Kondo, Tokyo, both of Japan

[73] Assignee: Centeon Pharma GmbH, Marburg, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/659,212

[22] Filed: Jun. 5, 1996

[30] Foreign Application Priority Data

Jun. 5, 1995 [JP] Japan ..................................... 7-137863

[51] Int. Cl.$^7$ ............................. A61K 35/14; A01N 1/02; C12P 21/06
[52] U.S. Cl. ............................. 530/381; 530/382; 435/2; 435/69.1; 435/69.6; 424/529; 424/530; 424/531; 436/69
[58] Field of Search ..................................... 424/101, 177, 424/105, 529, 530, 531, 94.64, 94.3; 530/380, 381, 399, 384, 382; 435/212, 16, 188, 2, 69.1, 69.6; 514/802

[56] References Cited

U.S. PATENT DOCUMENTS

| | | | |
|---|---|---|---|
| 4,327,086 | 4/1982 | Fukushima et al. | 424/177 |
| 4,470,968 | 9/1984 | Mitra et al. | 424/101 |
| 5,204,447 | 4/1993 | Bishop et al. | 530/381 |
| 5,612,456 | 3/1997 | Bishop et al. | 530/381 |

OTHER PUBLICATIONS

Bishop et al. "Human Recombinant Factor XIII from Saccharomyces cerevisiae". Journal of Biological Chemistry. vol. 265, No. 23:13888–13889, 1990.

*Primary Examiner*—Louise N. Leary
*Attorney, Agent, or Firm*—Finnegan, Henderson, Farabow, Garrett & Dunner, L.L.P.

[57] ABSTRACT

A stabilized aqueous liquid preparation of human blood coagulation factor XIII, prepared by recombinant DNA technology, from the group consisting of galactose, sucrose, sorbitol, glutamate, aspartate and histidine and where little reduction in biological activity occurs even when stored for a longer time.

18 Claims, No Drawings

STABILIZED AQUEOUS LIQUID PREPARATIONS OF BLOOD COAGULATION FACTOR XIII

BACKGROUND OF THE INVENTION

1. Field of the Invention

The present invention relates to a stabilized aqueous liquid preparation of human blood coagulation factor XIII, prepared by recombinant DNA technology, which comprises as a stabilizer at least one element selected from the group consisting of galactose, sucrose, sorbitol, glutamates, aspartates and histidine.

2. Description of the Related Art

Human blood coagulation factor XIII (hereinafter referred to as "factor XIII") exists widely in human blood plasma or human placenta, and is activated by thrombin and $Ca^{2+}$ forming $\epsilon$-($\gamma$-glutamyl)lysine bonds among various proteins to cross-link the molecules cross-linked. Dimerization of fibrin $\gamma$-chain and polymerization of fibrin $\alpha$-chain by this active type factor XIII give fibrin strength and elasticity and pertains to the hemostatic mechanism. Further, this active type factor XIII catalyzes cross-linking of fibronectin to fibrin $\alpha$-chain or collagen and plays an important role in the process of wound healing [Matsuda, NIPPON KETSUEKI GAKKAI ZASSHI, Vol 40, No. 6, pp 995–1002, (1977)].

SUMMARY OF THE INVENTION

Factor XIII is extracted, purified and isolated from human placenta or human plasma and may be formed into a pharmaceutical preparation through pasteurization (heated at 60° C. for a period of 10 hours in an aqueous solution) to inactivate various viruses (retroviruses such as hepatitis virus B, HIV-1 and others). It is generally known that factor XIII tends to decrease its activity during the production process and in storage. In particular, it is known that 1.0–3.0 M amino acids or 20–60 w/w% monosaccharides or oligosaccharides can be added as a stabilizer in view of the remarkable decrease in its activity during pasteurization (U.S. Pat. No. 4,297,344). When factor XIII is stored in a liquid form, the stability is poor. Hence, human serum albumin and glucose are added as stabilizers for storage; thereafter, freeze-drying is done. Presently, it has been marketed in the form of a freeze-dried preparation packed with the water for injection according to the Pharmacopoeia of Japan (JP) in order to make a solution therefor. This type of form is troublesome in that physicians need to dissolve the freeze-dried preparation in the water for injection just before administration to patients and further it requires time for dissolution to obtain a homogeneous solution, which has presented a major problem in administering the preparation to patients in emergency.

Factor XIII produced according to recombinant DNA technology does not need any sterilization by heating as it contains no pathogens such as viruses and others, but an aqueous solution thereof is unstable.

Thus, it is an object of this invention to provide a stabilized aqueous liquid preparation wherein factor XIII can be stored in the form of an aqueous liquid over a prolonged period of time without any need for lyophilization.

Means for Solving the Problem

The present invention is directed to a stabilized aqueous liquid preparation of human blood coagulation factor XIII, prepared by recombinant DNA technology, characterized in that the preparation comprises as a stabilizer at least one element selected from the group consisting of galactose, sucrose, sorbitol, glutamates, aspartates and histidine.

Examples of the stabilizer usable in the present invention include galactose, sucrose, sorbitol, glutamates, aspartates and histidine. These are used singly or in combination of two or more. Preferable glutamates and aspartates are their alkali metal salts and alkaline earth metal salts; their examples include salts of potassium, sodium and magnesium. Glycine, alanine, hydroxyproline, glutamine, $\alpha$-, $\beta$-, and $\gamma$-aminobutyrates, and glucose, which are used in heating and disinfection of natural factor XIII when extracted and refined from human placenta or human blood plasma, have been unexpectedly ineffective as the storage stabilizer for the factor XIII prepared by recombinant DNA technology.

The factor XIII to be stabilized according to the present invention is factor XIII prepared by recombinant DNA technology as well as its homologues having blood-coagulation activity. Examples of such factor include the factor XIII described in DE 3804890A1, an amino acid sequence of which is based on the amino acid sequence of the factor XIII described in FIG. 3 of the report of Grundmann et al., Natl. Acad. Sci. USA Vol. 83, pp. 8024–8028 (1986), incorporated by reference herein and has the amino acid sequence from No. 1 Ser through No. 731 Met of the FIG. 3, and has Phe in place of No. 88 Leu of the FIG. 3.

The DNA sequence encoding the above-mentioned amino acid sequence is inserted between Sst I and Hind III, polylinker sites, of pEMBLyex4 (J. K. Selton, Genetic Engineering (1987), Plenum Publishing Co., vol. 9, pp. 134–154), which is an expression vector of yeast; thereby, a plasmid for preparing factor XIII is formed. By use of the resulting plasmid, CL3ABYS86 (DE 3804890A1 incorporated by reference herein), which is a yeast host, is transformed to produce recombinant factor XIII in yeast; the recombinant factor XIII is purified from the supernatant in which the yeast is destroyed; and thereby, an extract liquid containing biologically active factor XIII is obtained.

Homologue herein means what is modified from the amino acid sequence of factor XIII by replacement, deletion or addition; thus, proteins having sequences equivalent to the amino acid sequence of factor XIII are naturally included in the homologues. Furthermore, homologue may be also defined as a protein having a main part of the amino acid sequence in a way wherein main properties of factor XIII are maintained.

Pharmaceutical preparation of factor XIII is currently administered by intravenous injection as a freeze-dried preparation for the improvement of bleeding tendency caused by congenital lack of blood-coagulation factor XIII, therapy of ruptured suture and fistula by decrease of blood-coagulation factor XIII, and symptom improvement of Schoenlein-Henoch purpura. Judging from the administered cases, not less than 20,000 in Japan and abroad, and from the acute toxicity test shown in Table 1, there is usually no need of concern for side effects and toxicity when the administration amount is 20–50 units/kg/person/day.

TABLE 1

| Animal | Administration | Sex | $LD_{50}$ (unit/kg) |
| --- | --- | --- | --- |
| Mouse (NMR 1 strain) 10 males and 10 females/group | i.v. | Male Female | >3,125 |

TABLE 1-continued

| Animal | Administration | Sex | LD$_{50}$ (unit/kg) |
|---|---|---|---|
| Wistar rat 10 males and 10 females/group | i.v. | Male Female | >625 |

The liquid preparation of the present invention may be administered in various forms in the same way as a freeze-dried preparation; it may be administered intravenously, hypodermically and intramuscularly, and preparation for external application to the skin may be administered as well. The liquid preparation of the present invention should be preferably stored in a dark cold place in the same way as a freeze-dried preparation; storage at nearly 4° C. is preferable.

For the purpose of the present invention, sucrose, D-sorbitol, sodium L-glutamate, sodium L-aspartate and L-histidine were respectively added to an aqueous solution of factor XIII (adjusted to a final titer of 100 units/ml) prepared by the recombinant DNA technology mentioned above; then the optimum concentration was studied for respective cases. Referring to the results of these studies, severe tests were made for liquid preparations in which the solutions listed below were added respectively to the factor XIII (adjusted to a final titer of 100 units/ml) for determining the activity change of factor XIII: 20% D-sorbitol; 15% sucrose; 0.5% sodium L-glutamate; 1% sodium L-aspartate; 1% L-histidine; 20% D-sorbitol plus 0.5% sodium L-glutamate, 20% D-sorbitol plus 1% sodium L-aspartate; 20% D-sorbitol plus 1% L-histidine; 15% sucrose plus 0.5% sodium L-glutamate; 15% sucrose plus 1% sodium L-aspartate; 15% sucrose plus 1% L-histidine; and, as a control, the water for injection according to the Pharmacopoeia of Japan. The results showed nearly 100% maintenance by the addition of the stabilizers according to the present invention.

Furthermore, for the purpose of the present invention, to factor XIII (adjusted to a final titer of 100 units/ml) prepared by the recombinant DNA technology mentioned above was added, 0.5% sodium L-glutamate, 15% sucrose plus 1% sodium L-aspartate, 15% sucrose plus 1% L-histidine, and, as a control, the water for injection according to the Pharmacopoeia of Japan respectively; the respective solutions were subjected to acceleration tests for predicting the long term change of factor XIII activity. No deterioration of the factor XIII activity was shown by the addition of the stabilizers according to the present invention.

As for the measuring methods of factor XIII activity, fibrin formation, transglutaminase activity measurement, and immunologic measurement of antigen amount can be mentioned. Herein, the dansylcadaverine method (Nishida J., et al. Thromb. Res., vol. 36 pp. 123–131 (1984)) was adopted which can determine quantitatively the active factor XIII with high accuracy. Dansylcadaverine (purchased from YATRON) is a fluorescent amine which is the substrate of factor XIII, and forms dansylcadaverine-casein complex with casein by the action of factor XIII; the complex is separated by gel-filtration after the reaction and the factor XIII activity can be determined by the fluorescence intensity of the complex. The factor XIII activity is expressed by units; one unit is the amount of factor XIII which is contained in one milliliter of normal human plasma.

In the pharmaceutical preparation, galactose, sucrose or sorbitol is used in a concentration of 1.25 to 40 percent, preferably 10 to 20 percent, weight to volume (w/v %). The amino acid is effective when used in a concentration of 0.125 to 20 w/v %, preferably 0.5 to 2 w/v %. Factor XIII is used in a concentration of 1 to 2,500 units/ml, preferably 60 to 200 units/ml. A pH adjuster and an osmotic pressure adjuster for isotonization may be incorporated into the pharmaceutical preparation of the present invention. The pH of the pharmaceutical preparation of the present invention preferably ranges from 6 to 9, most preferably ranges from 7 to 8.

EXAMPLES

Now, the present invention is illustrated more specifically by way of examples and formulation examples. However, these examples and formulation examples do not limit the scope of the present invention.

Example 1

Optimum concentration of the present stabilizers was investigated.

To factor XIII produced according to the recombinant DNA technology as disclosed in DE 3804890 A1 and incorporated by reference herein, (adjusted to the final titer of 100 units/ml with the water for injection according to the Pharmacopoeia of Japan) was added galactose, sucrose, D-sorbitol, sodium L-glutamate, sodium L-aspartate or L-histidine, and the mixture was warmed in a hot water bath at 60° C. for 30 minutes and then the activity of factor XIII was determined. Residual activity rate (%) of factor XIII was calculated, defining as 100% factor XIII activity of the preparation wherein factor XIII solution was adjusted to a titer of 100 units/ml.

A concentration of galactose, sucrose or sorbitol may be effectively 1.25–40 w/v %, 10–20 w/v % being particularly preferred. A concentration of amino acid may be effectively 0.125–10 w/v %, 0.5–2 w/v % being particularly preferred. On the basic of the above results, the following formulation examples were prepared.

TABLE 2

| | Residual Activity Rate (%) | | | | |
|---|---|---|---|---|---|
| Additive Conc. (w/v %) | Sucrose | D-Sorbitol | Sodium L-glutamate | Sodium L-aspartate | L-Histidine |
| 0 | 61.2 | 61.2 | 61.2 | 61.2 | 61.2 |
| 0.125 | | | 76 | 83.3 | 62.2 |
| 0.25 | | | 71.1 | 80.9 | 71.6 |
| 0.5 | | | 98.6 | 93.3 | 78.4 |
| 1.0 | | | 92.5 | 101.1 | 97.4 |
| 1.25 | 86.7 | 73.8 | | | |
| 2.0 | | | 87.8 | 66.5 | 65.3 |
| 2.5 | 88.6 | 73.9 | | | |
| 5.0 | 90.0 | 74.5 | 79.4 | 58.8 | |
| 10 | 99.0 | 94.0 | 65.3 | 55.4 | |
| 15 | 100.0 | 98.4 | | | |
| 20 | 96.2 | 96.0 | | | |
| 40 | 75.7 | 86.9 | | | |

Formulation Example 1

The purified recombinant factor XIII was adjusted to a titer of 200 units/ml and admixed with a 40% D-sorbitol solution in equal volumes to prepare a liquid preparation having the final titer of factor XIII of 100 units/ml and containing a 20% D-sorbitol solution.

Formulation Examples 2–13

The stabilizers as indicated in Table 2 were used in the same manner as described in Formulation Example 1 to prepare the liquid preparations having the final titer of factor XIII of 100 units/ml and containing the solutions of saccharides, sugar alcohol and amino acids with the concentrations as indicated in Table 2.

Example 2

Severe Test

The preparations of the Formulation Examples 1–13 were heated in a hot water bath at 60° C. for 30 minutes and then factor XIII activity was determined. Residual activity rate (%) of factor XIII was calculated, defining as 100% factor XIII activity in the preparation wherein the recombinant factor XIII solution was adjusted to a titer of 100 units/ml. The results are shown in Table 3.

Inactivation of factor XIII by heating at 60° C. for 30 minutes was prevented by the addition of saccharides, sugar alcohol and amino acids. Approximately 100% activity was retained.

TABLE 3

| Formulation Example | Additive | Residual activity rate (%) |
|---|---|---|
| 1 | 20% D-sorbitol | 96.0 |
| 2 | 15% sucrose | 99.0 |
| 3 | 0.5% sodium L-glutamate | 98.6 |
| 4 | 1% sodium L-aspartate | 101.1 |
| 5 | 1% L-histidine | 97.4 |
| 6 | 20% D-sorbitol + 0.5% sodium L-glutamate | 97.3 |
| 7 | 20% D-sorbitol + 1% sodium L-aspartate | 99.6 |
| 8 | 20% D-sorbitol + 1% L-histidine | 101.0 |
| 9 | 15% sucrose + 0.5% sodium L-glutamate | 101.5 |
| 10 | 15% sucrose + 1% sodium L-aspartate | 100.9 |
| 11 | 15% sucrose + 1% L-histidine | 100.5 |
| 12 | 1% L-lysine L-glutamate dihydrate | 84.0 |
| 13 | 0.5% galactose | 87.5 |
| Control | water for injection (Pharmacopoeia of Japan) | 61.2 |

As is apparent from the results of Table 3, a stable solution having factor XIII residual activity of 84% or more was obtained by the addition of at least one of the present stabilizers to a solution of the biologically active factor XIII produced using recombinant DNA technology. As stated above, a stable and highly safe liquid preparation which comprises, as an active ingredient, biologically active factor XIII could be obtained by the addition of at least one of the present stabilizers.

Example 3

Acceleration Test

The formulations of the Formulation Examples 3, 10 and 11 were stored at 40° C. At the commencement of storage and the first, second and third months, samples were collected and residual activity rate (%) of factor XIII was calculated. The 15 results are shown in Table 4.

TABLE 4

| Formulation Example | Additive | Residual activity rate (%) | | | |
|---|---|---|---|---|---|
| | | Started | 1st month | 2nd month | 3rd month |
| 3 | 0.5% sodium L-glutamate | 100 | 99.5 | 91.6 | 96.1 |

TABLE 4-continued

| Formulation Example | Additive | Residual activity rate (%) | | | |
|---|---|---|---|---|---|
| | | Started | 1st month | 2nd month | 3rd month |
| 10 | 15% sucrose + 1% sodium L-aspartate | 100 | 93.0 | 32.4 | 91.9 |
| 11 | 15% sucrose + 1% L-histidine | 100 | 99.2 | 99.8 | 95.5 |
| Control | water for injection (Pharmacopoeia of Japan | 100 | 76.8 | 46.0 | 7.8 |

As shown in Table 4, the Control, the liquid preparation of 20 factor XIII produced according to recombinant DNA technology containing no stabilizer, showed a lowered activity with aging during the storage at 40° C. On the other band, the aqueous liquid preparations having incorporated therein at least one of the present stabilizers showed the residual activity of factor XIII of 90% or more after 3 months at 40° C.

Accordingly, this invention provides for a stable and safe aqueous liquid preparation comprising as an active ingredient factor XIII by the addition of at least one element selected from galactose, sucrose, sorbitol, glutamate, aspartate and histidine. In this way, the preparation may be stored in a liquid state over a prolonged period of time, while maintaining its biological activity, and because there is no need for redissolution like the freeze-dried preparation, clinical physicians will be saved from the difficulties of administering the freeze-dried preparation to patients.

We claim:

1. A stabilized aqueous liquid preparation which comprises blood coagulation Factor XIII obtained by recombinant DNA technology, wherein said Factor XIII in said liquid preparation is biologically active and is free of pathogens without heating or pasteurization, and which further comprises at least one element selected from the group consisting of galactose, sucrose, glutamate, aspartate and histidine as a stabilizer to produce said stabilized aqueous liquid preparation.

2. The stabilized aqueous liquid preparation which comprises blood coagulation factor XIII as claimed in claim 1, and at least two elements selected from the group consisting of sucrose, sorbitol, glutamate, aspartate and histidine as a stabilizer.

3. A stabilized aqueous liquid preparation which comprises a blood coagulation factor XIII homologue which exhibits the biological activity of factor XIII, obtained by recombinant DNA technology and at least one element selected from the group consisting of galactose, sucrose, sorbitol, glutamate, aspartate and histidine as a stabilizer, wherein the factor XIII homologue maintains the biological activity of factor XIII.

4. An aqueous liquid preparation which comprises an effective amount of a blood coagulation factor XIII homologue which exhibits the biological activity of factor XIII, as claimed in claim 3, and at least one element selected from the group consisting of sucrose, sorbitol, glutamate, aspartate and histidine as a stabilizer.

5. An aqueous liquid preparation which comprises an effective amount of a blood coagulation factor XIII homologue which exhibits the biological activity of factor XIII, as claimed in claim 3, and at least one element selected from the group consisting of sucrose and glutamate, aspartate and histidine as a stabilizer.

6. An aqueous liquid preparation which comprises an effective amount of a blood coagulation factor XIII homologue which exhibits the biological activity of factor XIII, as claimed in claim 3, and at least one element selected from the group consisting of sorbitol and glutamate, aspartate and histidine as a stabilizer.

7. The stabilized aqueous liquid preparation which comprises blood coagulation factor XIII as claimed in claim 1 or claim 2, and glutamate as a stabilizer.

8. The stabilized aqueous liquid preparation which comprises blood coagulation factor XIII as claimed in claim 1 or claim 2, and sucrose and glutamate as a stabilizer.

9. The stabilized aqueous liquid preparation which comprises blood coagulation factor XIII as claimed in claim 1 or claim 2, and sucrose and aspartate as a stabilizer.

10. The stabilized aqueous liquid preparation which comprises blood coagulation factor XIII as claimed in claim 1 or claim 2, and sucrose and histidine as a stabilizer.

11. A method of preparing a stabilized aqueous liquid preparation which comprises obtaining blood coagulation factor XIII by recombinant DNA technology and adding at least one element selected from the group consisting of galactose, sucrose, glutamate, aspartate and histidine as a stabilizer to produce said stabilized aqueous liquid preparation.

12. The method of preparing a stabilized aqueous liquid preparation which comprises blood coagulation factor XIII as claimed in claim 11, and two elements selected from the group consisting of sucrose, sorbitol, glutamate, aspartate and histidine as a stabilizer.

13. The method of preparing a stabilized aqueous liquid preparation which comprises blood coagulation factor XIII as claimed in claim 11, and glutamate as a stabilizer.

14. The method of preparing a stabilized aqueous liquid preparation which comprises blood coagulation factor XIII as claimed in claim 11, and sucrose and glutamate as a stabilizer.

15. The method of preparing a stabilized aqueous liquid preparation which comprises blood coagulation factor XIII as claimed in claim 11, and sucrose and aspartate as a stabilizer.

16. The method of preparing a stabilized aqueous liquid preparation which comprises blood coagulation factor XIII as claimed in claim 11, and sucrose and histidine as a stabilizer.

17. A method which comprises administering to a person having a deficiency of factor XIII 20–50 units/kg/person/day of the stabilized aqueous liquid preparation of claim 1 to remedy the deficiency.

18. A stabilized aqueous liquid preparation which comprises blood coagulation factor XIII obtained by recombinant DNA technology and which further comprises at least one element selected from the group consisting of galactose, sucrose, sorbitol, glutamate, aspartate and histidine as a stabilizer, said factor XIII being stabilized for storage in an aqueous solution.

\* \* \* \* \*

UNITED STATES PATENT AND TRADEMARK OFFICE
CERTIFICATE OF CORRECTION

PATENT NO.    : 6,084,074
DATED         : July 4, 2000
INVENTOR(S)   : Naoko Kato et al.

It is certified that error appears in the above-identified patent and that said Letters Patent is hereby corrected as shown below:

<u>Title page,</u>
Item [73], Assignee, add -- [73]: Hoechst Japan Ltd., Tokyo, Japan --

Signed and Sealed this

Twenty-second Day of October, 2002

Attest:

Attesting Officer

JAMES E. ROGAN
*Director of the United States Patent and Trademark Office*